United States Patent
Buckley et al.

(10) Patent No.: US 9,107,770 B2
(45) Date of Patent: Aug. 18, 2015

(54) ENDOPROSTHESIS WITH VARYING COMPRESSIBILITY AND METHODS OF USE

(71) Applicant: W. L. Gore & Associates, Inc., Newark, DE (US)

(72) Inventors: Kyle R. Buckley, Flagstaff, AZ (US); Benjamin I. Espen, Flagstaff, AZ (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 66 days.

(21) Appl. No.: 13/740,434

(22) Filed: Jan. 14, 2013

(65) Prior Publication Data

US 2013/0211498 A1    Aug. 15, 2013

Related U.S. Application Data

(60) Provisional application No. 61/598,777, filed on Feb. 14, 2012.

(51) Int. Cl.
| | |
|---|---|
| *A61F 2/91* | (2013.01) |
| *A61F 2/82* | (2013.01) |
| *A61F 2/07* | (2013.01) |
| *A61F 2/954* | (2013.01) |
| *A61F 2/97* | (2013.01) |

(Continued)

(52) U.S. Cl.
CPC ... *A61F 2/82* (2013.01); *A61F 2/07* (2013.01); *A61F 2/954* (2013.01); *A61F 2/97* (2013.01); *A61F 2/89* (2013.01); *A61F 2002/065* (2013.01); *A61F 2002/072* (2013.01); *A61F 2002/075* (2013.01); *A61F 2250/0018* (2013.01); *A61F 2250/0029* (2013.01)

(58) Field of Classification Search
CPC ..................................... A61F 2/82; A61F 2/91
USPC ................................................ 623/1.35–1.48
See application file for complete search history.

(56) References Cited

U.S. PATENT DOCUMENTS

| | | | | |
|---|---|---|---|---|
| 7,213,495 | B2 * | 5/2007 | McCullagh et al. | 87/9 |
| 8,496,698 | B2 * | 7/2013 | Abunassar | 623/1.15 |

(Continued)

FOREIGN PATENT DOCUMENTS

| | | |
|---|---|---|
| EP | 1 666 003 | 6/2006 |
| WO | 95/18585 | 7/1995 |

(Continued)

OTHER PUBLICATIONS

International Search Report and Written Opinion for PCT/US2013/021520 mailed Feb. 28, 2013.

*Primary Examiner* — Suzette J Gherbi
(74) *Attorney, Agent, or Firm* — Gilbert R. Gabo

(57) ABSTRACT

The present disclosure is directed to an endoprosthesis comprising a graft component and at least one support component with varying compressibility along the length of the endoprosthesis. In various embodiments, the endoprosthesis comprises at least a first segment and a second segment, wherein the first segment is more compressible than the second. In another embodiment having a second segment between the first and third segments, the third segment can also be more compressible than the second segment. Alternatively, in an embodiment, a second segment can have greater rigidity than a first segment, as well as a third segment, if present.

24 Claims, 8 Drawing Sheets

(51) Int. Cl.
*A61F 2/06* (2013.01)
*A61F 2/89* (2013.01)

(56) References Cited

U.S. PATENT DOCUMENTS

| | | | |
|---|---|---|---|
| 2005/0143806 A1* | 6/2005 | Phillips | 623/1.23 |
| 2007/0010872 A1* | 1/2007 | Gregorich | 623/1.16 |
| 2009/0163994 A1 | 6/2009 | Quigley et al. | |
| 2009/0306762 A1* | 12/2009 | McCullagh et al. | 623/1.13 |
| 2010/0312329 A1* | 12/2010 | Lowe et al. | 623/1.16 |
| 2011/0230957 A1* | 9/2011 | Bonsignore et al. | 623/1.16 |
| 2013/0261727 A1* | 10/2013 | Perkins et al. | 623/1.12 |
| 2013/0274868 A1* | 10/2013 | Cox et al. | 623/1.39 |
| 2013/0304195 A1* | 11/2013 | Abunassar | 623/1.16 |

FOREIGN PATENT DOCUMENTS

| | | |
|---|---|---|
| WO | 2005/034807 | 4/2005 |
| WO | 2009/058369 | 5/2009 |

\* cited by examiner

ENDOPROSTHESIS WITH VARYING COMPRESSIBILITY AND METHODS OF USE

CROSS-REFERENCE TO RELATED APPLICATION

This U.S. Non-Provisional patent application claims priority to and the benefit of U.S. Provisional Patent Application Ser. No. 61/598,777 entitled ENDOPROSTHESIS WITH VARYING COMPRESSIBILITY OR RIGIDITY AND METHODS OF USE and filed Feb. 14, 2012, which is incorporated by reference herein in its entirety.

FIELD

The present disclosure relates to improved endoprostheses for treating disease of the vasculature, and more specifically, to stent grafts having varying compressibility.

DISCUSSION OF THE RELATED ART

An endovascular stent graft can be used to treat an aortic aneurysm or other vascular trauma by delivering the graft to the aneurysm through an iliac artery. The graft is packaged tightly in an outer tube or sheath and deployed into the aorta to bypass the aneurysm using, inter alia, X-ray guidance and a series of catheters and guidewires. The outer tube or sheath is withdrawn, the graft is expanded, and the aneurysm is thereby treated.

Many complexities arise in this procedure. First, the inherent limitations of an endoscopic procedure as compared to an open-surgery make it more difficult to precisely position the graft during implantation. For precise positioning, a rigid graft can be desirable to enable better torqueability and pushability. On the other hand, the graft has to properly seal above and below the aneurysm to prevent the flow of blood outside the graft and into the aneurismal sac. In this regard, a compressible graft can be desirable to enable better conformability and improved adaptability to tortuous vasculature and patients' unique anatomies.

These issues are magnified even more when, as is the case with aortic aneurysms, a bifurcated stent graft is being implanted. For example, a bifurcated stent graft used in the treatment of abdominal aortic aneurisms can be inserted through an iliac artery up into the abdominal aorta where it is deployed and anchored. The graft's ipsilateral leg extends down into the iliac artery through which the graft was inserted. On the other hand, the graft's contralateral leg does not extend below the abdominal aorta. To extend the graft's contralateral leg down into the other iliac artery, a second stent graft is inserted through that other iliac artery over a guidewire and attached to the original graft's contralateral leg.

For this second graft to be successfully deployed, the opening of the graft's contralateral leg needs to be aligned with the passage way into the other iliac artery. Fine-rotational tuning of the bifurcated graft's position is required to achieve this alignment. Additionally, branched vessels are by definition very tortuous and in these areas, more variations exist in a patient's unique anatomy.

Therefore, there exists a need for a stent graft that can provide adequate rigidity during deployment for pushability and torqueability, but also flexibility so that the stent graft is adaptable to a patient's unique anatomical variations and tortuous vasculature and is conformable thereto to ensure proper sealing of the stent graft.

BRIEF DESCRIPTION OF THE DRAWINGS

The accompanying drawings are included to provide a further understanding of the disclosure and are incorporated in and constitute a part of this specification, illustrate embodiments of the disclosure and together with the description serve to explain the principles of the disclosure, wherein.

DETAILED DESCRIPTION

Figure 1A:
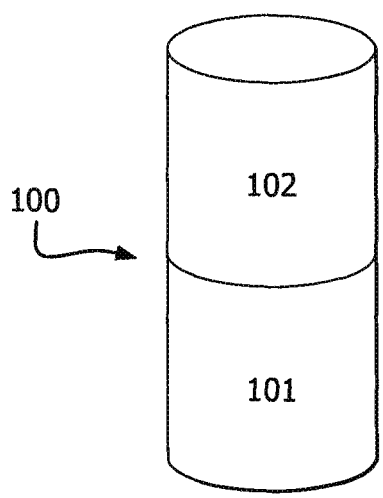
FIG. 1(a) illustrates an embodiment comprising two segments of varying compressibility or rigidity.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. As used herein, "secure" means to couple, join, connect, attach, or secure two or more elements whether directly or indirectly whether permanently or temporarily. Finally, although the present disclosure can be described in connection with various principles and beliefs, the present disclosure should not be bound by theory.

In addition, the present disclosure will be described primarily with reference to treating disease of the abdominal aorta, however, the disclosure and principles can be applied to other disease of the vasculature, including, for example, any disease where a branched or non-branched vessel is to be treated. Likewise, although the disclosure will be described primarily with reference to bifurcated endoprostheses, it should be understood that the disclosure and principles can be applied to endoprostheses having no branches or any number of branches, for example, 2, 3, 4 or more.

As used herein, the term "elongate member" includes any longitudinally extending structure with or without a lumen therethrough. Thus, elongate members include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Elongate members can be of any material and can have any cross-sectional shape including but not limited to profiles that are circular, oval, triangular, square, polygon shaped or randomly shaped.

As used herein, the terms "compressibility" and "rigidity" refer to column strength or the extent of susceptibility or resistance to axial elongation, axial shortening, bending, or other deformation. When using both of the terms "compressibility" and "rigidity" to describe a particular embodiment, the purpose is for making a relative comparison. In this regard, a compressible element will generally be more susceptible to axial elongation, axial shortening, bending, or other deformation, whereas, a rigid element will generally be more resistant to axial elongation, axial shortening, bending, or other deformation.

The present disclosure is directed toward an endoprosthesis comprising a tubular member. The term "tubular member" includes any structure with a lumen therethrough. Tubular members can be of any material and can have any cross-sectional shape including but not limited to profiles that are circular, oval, triangular, square, polygon shaped or randomly shaped. An endoprosthesis can comprise at least two interconnected tubular members, e.g., a branched endoprosthesis. As used herein, a tubular member refers to both a single, unbranched tubular member and a plurality of interconnected tubular members.

Figure 1B:
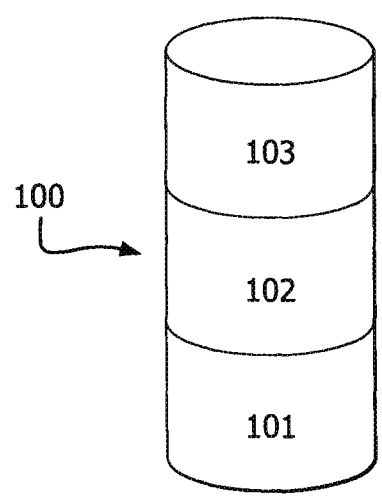
FIG. 1(b) illustrates an embodiment comprising three segments of varying compressibility or rigidity.

In an embodiment and with reference to FIG. 1(a), a tubular member 100 comprises first and second segments 101,102 of differing compressibility or rigidity. In yet another embodiment and with reference to FIG. 1(b), tubular member 100 comprises at least three segments 101,102,103 of differing compressibilities or rigidities. While tubular member 100 having 2-3 segments is disclosed herein, it should be understood that tubular member 100 can comprise any number of segments with differing compressibility or rigidity.

This variation in compressibility along the length of tubular member 100 allows for tubular member 100 to have both rigid and compressible characteristics, thereby improving the ability of tubular member 100 to be pushable, torqueable, conformable, and adaptable. By way of example, the compressibility of first segment 101 can allow for improved conformability to a vessel wall as well as improved adaptability to tortuous vasculature and patients' unique anatomies. On the other hand, the rigidity of second segment 102 can allow for pushability and torqueability so that tubular member 100 can be repositioned during deployment.

In various embodiments, a segment is compressible upon application of a compression force, much like a spring. However, unlike a spring, the segment remains in its compressed state upon removal of the compression force, though in alternative embodiments, the segment can regain its extended shape, similar to a spring.

Figure 2:
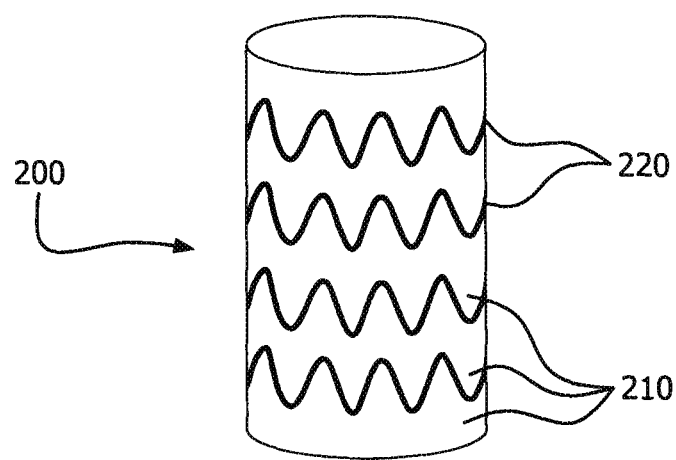
FIG. 2 illustrates an embodiment comprising a support component and a graft component.

In an embodiment and with reference to FIG. 2, a tubular member 200 can comprise a graft component 210 and at least one support component 220, such as in a stent graft. Graft component 210 and the at least one support component 220 together form tubular member 200. Graft component 210 is generally any abluminal (i.e., outer, vessel surface) or luminal (i.e., inner, blood flow surface) covering configured to partially or substantially couple to at least one lateral side of one or more support components 220.

In various embodiments, graft component 210 comprises ePTFE. However, other useful materials for graft component 210 can comprise one or more of nylons, polycarbonates, polyethylenes, polypropylenes, polytetrafluoroethylenes, polyvinyl chlorides, polyurethanes, polysiloxanes, and other biocompatible materials.

In an embodiment, graft component 210 will form at least one tuck or a series of tucks when a compressible segment is in its compressed state. A "tuck", as used herein, can comprise a folded or crumpled portion of graft component. The tuck can form on the abluminal or luminal side. In an embodiment, the tuck can be oriented to minimize fluid turbulence. While not required, pre-defined creases or pleats in the graft component can be used to facilitate the formation of tucks. The shape and configuration of the support component can also facilitate the formation of a tuck. Furthermore, the shape and configuration of the support component can hold a tuck along the abluminal or luminal surface of the tubular member.

In various embodiments, support component 220 has dimensions appropriate for the given treatment and can provide structural support for the graft component 210 of the endoprosthesis device and/or the vasculature to be treated. Support component 220 can comprise a stent. Support component 220 can be comprised of a shape-memory material, such as nitinol. In other embodiments, however, support component 220 can be comprised of other materials, self-expandable or otherwise expandable (e.g., with a conventional balloon catheter or spring mechanism), such as various metals (e.g., stainless steel), alloys and polymers.

In an embodiment, support component 220 can comprise any shape or configuration which provides the desired structural support for the graft component as well as the desired compressibility or rigidity. In an embodiment, support component 220 comprises serially aligned elements that together make support component 220. For example, the coils of a spiral or helix can be serially aligned; a series of tapering or symmetrical rings can be serially aligned; or substantially parallel strips or wires can be serially aligned. Another support component 220 can comprise a plurality of patterns cut from a tube and have any pattern suitable for the treatment with the desired compressibility. However, any shape or configuration of support component 220 which provides the desired structural support for graft component 210 as well as the desired compressibility, are suitable for use herein.

In an embodiment, a tubular member can comprise a plurality of support components 220 or a single support component 220. Likewise, each segment can comprise a single or a plurality of support components 220.

Support component 220 can comprise a stiffening member to hinder and resist compressibility of a segment. A stiffening member can be releasably attached so that the rigidity of a segment can be temporary. A stiffening member can be attached, releasable or otherwise, on the segment in which permanent or temporary rigidity is desired or at the distal ends thereof. A stiffening member will be sufficiently stiff so long as it impedes compression upon application of compression forces normally encountered during a treatment.

There are a number of other ways the support component 220 can be varied and adjusted to obtain the desired degree of compressibility. For example, the pitch of a spiral or helix or the space between neighboring rings can be selected to increase or decrease the compressibility. Likewise, selecting the material of which the support component is comprised for its flexibility or rigidity can contribute to the degree of compressibility or rigidity of a support component. Support component 220 can be varied and adjusted in any manner to obtain desired degree of support for the graft component and the desired degree of compressibility.

In an embodiment, structural variations in shape can be incorporated onto the support component 220 to further refine and obtain the desired degree of support for graft component 210 and the desired degree of compressibility. Similarly, structural variations can further facilitate or hinder the formation of tucks. For example, with reference to FIG. 3, an undulation 330 is a structural variation which can be used to impact compressibility in a variety of manners, as well as improve the conformability of the endoprosthesis 300 against a vessel wall. Undulation 330 is an up-and-down shape such that a series of which forms a sinusoidal or non-sinusoidal pattern. The amplitude of a series 331 of undulations 330 can be increased or decreased to vary compressibility. Undulations 330 can be symmetrical and vertically aligned to facilitate the formation of tucks, as illustrated in compressible segment 301. On the other hand, unsymmetrical undulations or vertically skewed undulations can hinder the ability to form tucks. With these structural variations incorporated onto support component 220, a pattern may or may not emerge. However, any structural variations in shape can be incorporated onto support component 220 to further refine and obtain the desired degree of support for graft component 210 and compressibility.

In an embodiment, support component 220 comprises a pattern which can be defined by any variety of repeating features that affect the compressibility of the tubular member. Each segment with a different degree of compressibility can comprise a different pattern. A pattern can be defined by any one or more of the following: the extent to which support component is fixedly secured to the graft component; the distance between support component structural variations; the support component shape; the number, size, or amplitude of an undulation; the variation amongst a plurality of undulations; the degree of skew or alignment of undulations along a vertical axis; the flexibility or rigidity of the material of which the support component is comprised; the tuck density over the length of a segment in its compressed position; or combinations thereof.

Graft component 210 can be fixedly secured or otherwise coupled at a single or a plurality of locations to the abluminal or luminal surface of support component(s) 220, for example, using one or more of taping, heat shrinking, adhesion and other processes known in the art. The manner in and extent to which graft component 210 is fixedly secured or otherwise coupled to support component 210 is yet another factor that can affect the amount of compressibility of a tubular member segment. The extent to which support component 210 is fixedly secured can hinder or facilitate the formation of tucks when compressed. For example, the percentage of the support component's lateral surface area fixedly secured to the graft component is lower with increased compressibility. In an embodiment, wherein the support component comprises undulations, the support component is fixedly secured from the base of the undulation upwards toward the undulation peak. In this embodiment, the base-to-peak percentage that is fixedly secured decreases with increased compressibility.

In some embodiments, a plurality of graft components are used and can be coupled to both the abluminal and luminal surfaces of the support component(s), especially wherein less compressibility or more rigidity is desired. Similarly in other embodiments, a plurality of graft components "sandwich" support component(s), graft components being attached to each other.

Figure 3:
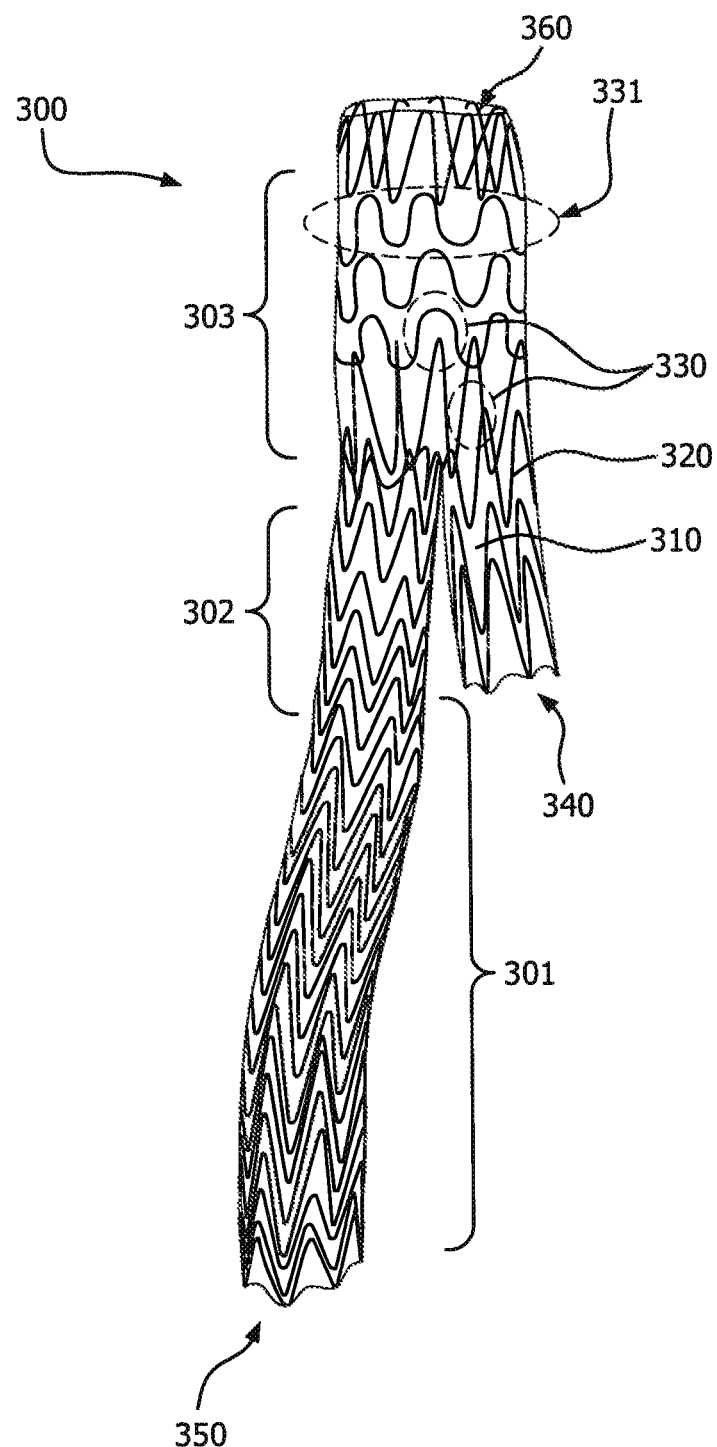
FIG. 3 illustrates an embodiment in which the support component has undulations and at least 3 segments of varying compressibility.

In various embodiments with reference to FIG. 3, endoprosthesis 300 comprises a body segment 303 and at least two leg segments 340 and 350.

The cross-section of the body segment 303 can be circular, ovoidal, or have polygonal features with or without curved features. The cross-sectional shape of the body segment 303 can be either substantially constant or variable along its axial length. In like manner, the cross-sectional surface area of the body segment 303 can be either substantially constant or variable along its axial length. In an embodiment of a bifurcated endoprosthesis 300, the body segment's cross-section is substantially circular at its distal end but tapers to have an ovoidal rectangular cross-section with a smaller cross-sectional surface area in its bifurcation region.

In this embodiment, endoprosthesis 300 comprises at least 3 segments of differing compressibility, compressible segment 301 and body segment 303 being more compressible than rigid segment 302.

In an embodiment, the support component of the body segment 303 comprises any shape and configuration such that the main body flexes, compresses, and is conformable to the vessel wall. For example, support component 320 of body segment 303 comprises a series 331 of undulations 330 only partially fixedly secured to graft component 310 to permit compressibility, flex, and conformability. However, support component 320 of body segment 303 of any shape and fixedly secured in any manner to improve the main body's compressibility and ability to flex and conform to the vessel wall is contemplated.

The main leg 350 of endoprosthesis 300 comprises compressible segment 301 and rigid segment 302. In an embodiment, the support component 320 of main leg 350 comprises an undulating helix. In compressible segment 301, the base-to-peak percentage of support component 320 that is fixedly secured to graft component 310 is less than that for rigid segment 302. The compressibility of compressible segment 301 and the undulating support component allows for, amongst other things, improved conformability to a vessel wall. On the other hand, most if not all of the lateral surface area of support component 320 in rigid segment 302 is fixedly secured to graft component 310 in order to have a higher degree of rigidity or lower compressibility. Alternatively, a stiffening member can be attached as described herein to obtain the desired rigidity. Such rigidity provides pushability and torqueability that allows endoprosthesis 300 to be repositioned during deployment.

In an embodiment, endoprosthesis 300 can further comprise an anchor 360 or plurality of anchors 360. Anchor 360 can comprise a barb or hook. Anchor 360 can be locatable on or near the distal end of endoprosthesis 300. Anchor 360 can be retractable for adjusting placement and repositioning of endoprosthesis 300. Endoprosthesis 300 can further comprise a constraining loop at the distal end to retract anchor 360.

Figure 4A:
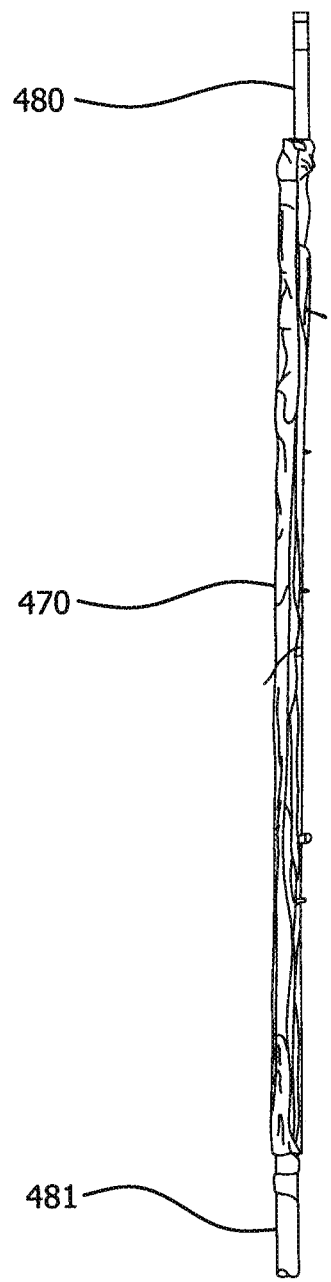
FIG. 4A illustrates an embodiment sheathed.

In an embodiment, the endoprosthesis comprises at least one removable sheath. The sheath facilitates endoprosthesis delivery through the vasculature. For example, and with reference to the accompanying drawings, FIG. 4A illustrates outer sheath 470 enclosing an endoprosthesis (not shown) as described herein to be delivered via a guidewire 480 and an elongate member 481. Sheath 470 can be comprised of one or more of nylons, polycarbonates, polyethylenes, polypropylenes, polytetrafluoroethylenes, polyvinyl chlorides, polyurethanes, polysiloxanes, stainless steels, or other biocompatible materials. In yet other embodiments, sheath 470 is a tubular element.

Additional features and elements can be used in connection with the present disclosure. In one embodiment for example, at least one leg is maintained in an open configuration for ease of cannulation. This can be accomplished, for example, by incorporating an independent wire or ring, such as a support component as described herein, at the distal end of the leg. In an embodiment, a plurality of serially aligned support components are adapted to hold the contralateral leg open for cannulation. In yet another embodiment, one or more radiopaque and/or echogenic markers are incorporated into the branched endoprosthesis, for example, along, or at the distal end of, the contralateral leg.

With reference to FIGS. 4A-4E, a cannulation method comprises delivering a bifurcated endoprosthesis 400 of varying compressibility as described herein enclosed by an outer sheath 470 into a branch artery and to the lumen of a trunk artery via a guidewire 480 and an elongate member 481.

Figure 4B:
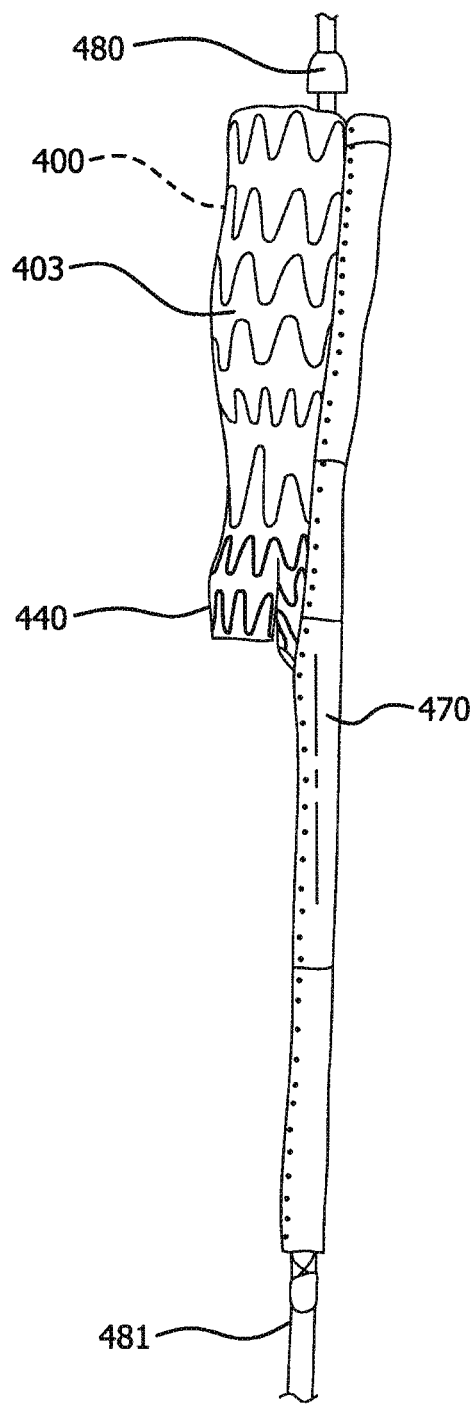
FIG. 4B illustrates an embodiment partially unsheathed.
Figure 4C:
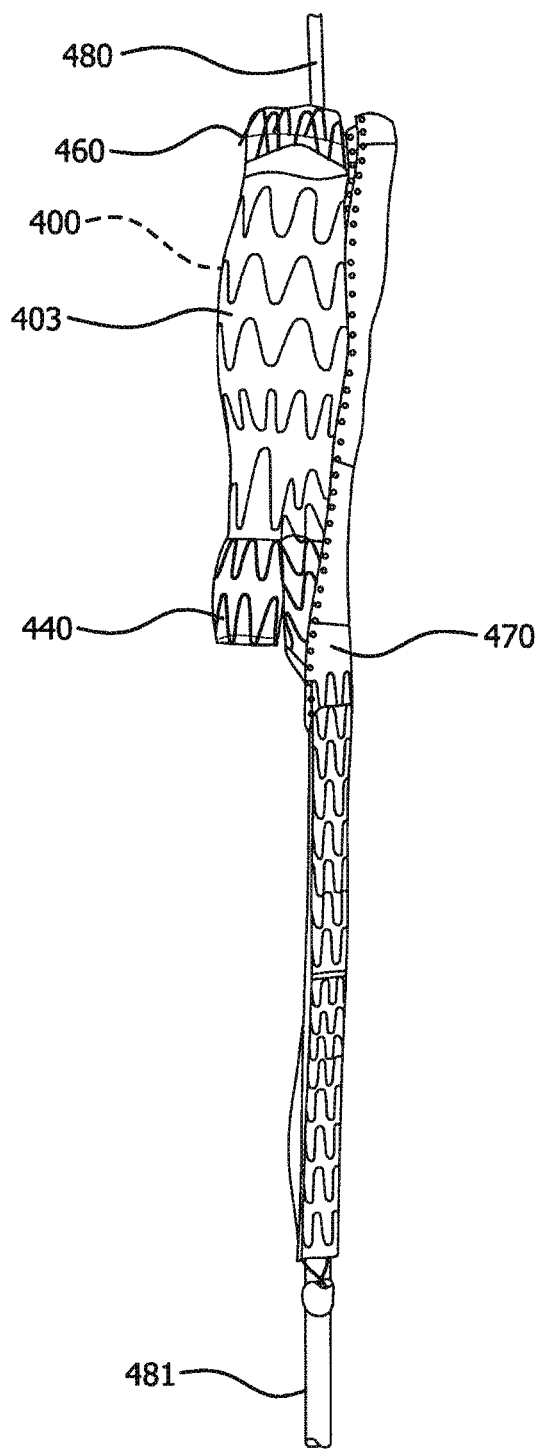
FIG. 4C illustrates an embodiment partially unsheathed with anchors retracted.

In various embodiments, with reference to FIG. 4B, the outer sheath 470 is partially removed from the body segment 403 of bifurcated endoprosthesis 400 extending into the trunk artery, thus partially deploying bifurcated endoprosthesis 400. Next, with reference to FIG. 4C, placement of bifurcated endoprosthesis 400 can be adjusted, for example, by retracting anchors 460 at the distal end of the body segment 403 of bifurcated endoprosthesis 400, rotating and/or advancing or reversing the guidewire 480 and/or the elongate member 481, and thereafter fully deploying the anchors 460 into the sides of the trunk artery. For purposes of positioning and repositioning, endoprosthesis rotation, advancement, or reversal as described above is more accurate when bifurcated endoprosthesis 400 comprises a rigid segment 402 of sufficient rigidity or minimal compressibility. The increased rigidity minimizes the degree of radial or axial deformation to rigid segment 402 while repositioning.

Once bifurcated endoprosthesis 400 is determined to be properly positioned, a second guidewire can be inserted into a contralateral leg 440 of the branched stent graft via a second branch artery in communication with the trunk artery. Cannulation of contralateral leg 440 can thereafter occur.

Figure 4D:
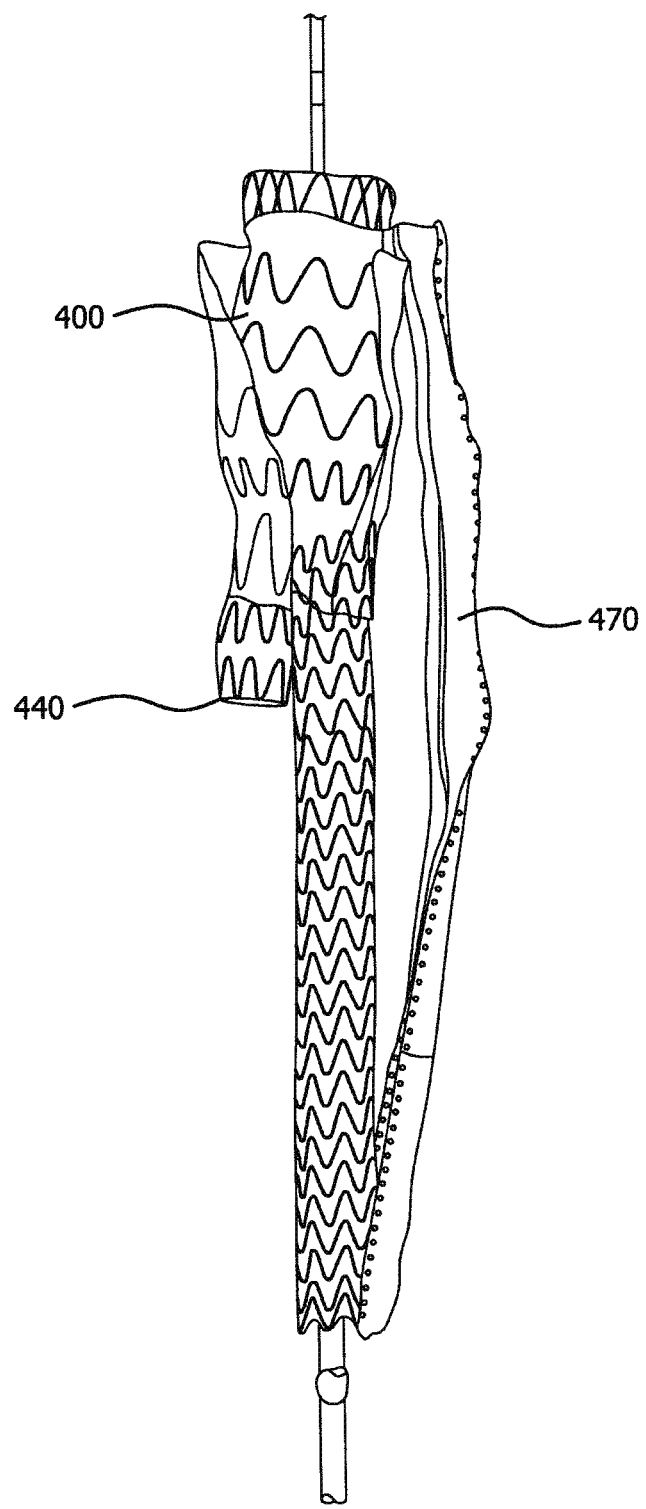
FIG. 4D illustrates an embodiment completely unsheathed.
Figure 4E:
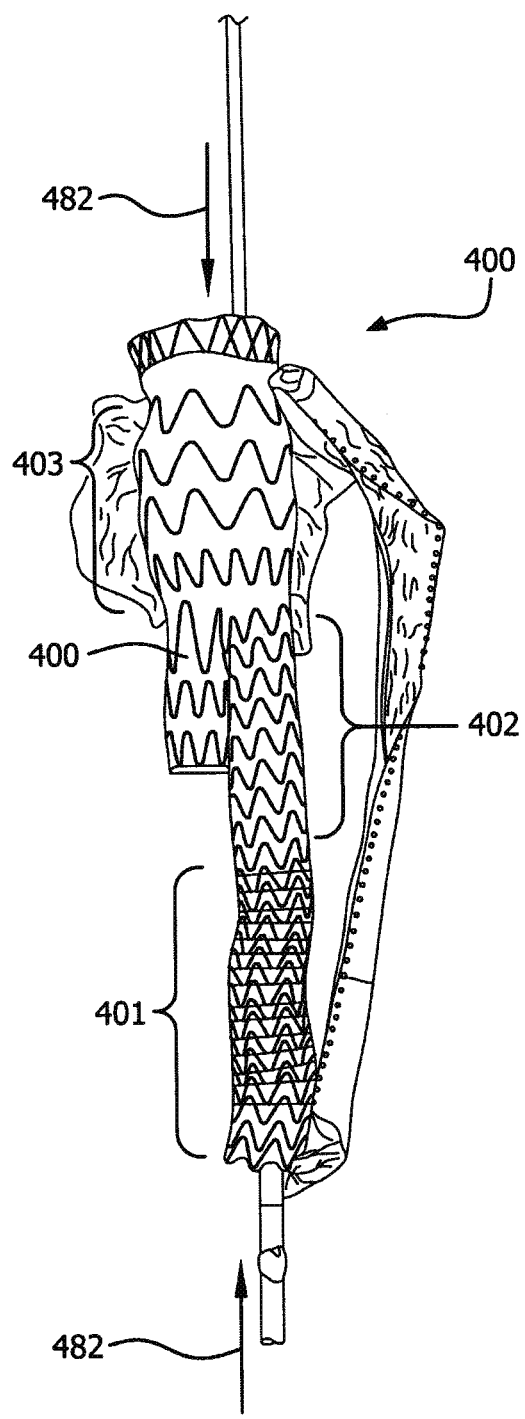
FIG. 4E illustrates an embodiment to which a longitudinal compression force is being applied.

Once the second guidewire has been inserted into contralateral leg 440 440, the outer sheath 470 can be fully removed as illustrated in FIG. 4D. Thereafter, with reference to FIG. 4E, a longitudinal compression force 482 can be applied to bifurcated endoprosthesis 400 to compress compressible segment 401 and/or body segment 403 to conform the bifurcated endoprosthesis 400 to the vessel walls.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An endoprosthesis comprising:
a graft component and a support component defining a lumen and comprising at least a first segment and a second segment,
wherein the lumen is continuous through the first segment and second segment, and
wherein the first segment has greater longitudinal compressibility than the second segment,
wherein the undulations along a vertical axis of the support component are more skewed in the second segment than in the first segment.

2. The endoprosthesis of claim 1 wherein the support component forms at least a first support component pattern in the first segment and a second support component pattern in the second segment.

3. An endoprosthesis of claim 1 wherein the support component comprises at least one of a helical member, a spiral member or a series of rings.

4. An endoprosthesis of claim 1 wherein the support component comprises a plurality of undulations.

5. An endoprosthesis of claim 1 wherein a percentage of lateral surface area of the support component that is fixedly secured to the graft component is lower in the first segment than in the second segment.

6. An endoprosthesis of claim 3 wherein a pitch of the helical member or a space between neighboring rings is greater in the first segment than in the second segment.

7. An endoprosthesis of claim 4 wherein a variation in amplitude amongst the undulations is greater in the second segment than in the first segment.

8. An endoprosthesis of claim 4 wherein the undulations along a vertical axis of the support component are more aligned in the first segment than in the second segment.

9. An endoprosthesis comprising:
a graft component and a support component defining a lumen and comprising at least a first segment, second segment, and a third segment,
wherein the lumen is continuous through the first segment, second segment, and the third segment, and
wherein the first and third segments have greater longitudinal compressibility than the second segment,
wherein a pitch of the helical member or a space between neighboring rings is greater in the first segment and third segment than in the second segment.

10. The endoprosthesis of claim 9 wherein the support component forms at least a first support component pattern in the first segment, a second support component pattern in the second segment and a third support component pattern in the third segment.

11. An endoprosthesis of claim 9 wherein the support component comprises at least one of a helical member, a spiral member or a series of rings.

12. An endoprosthesis of claim 9 wherein the support component comprises a plurality of undulations.

13. An endoprosthesis of claim 9 wherein a percentage of lateral surface area of the support component that is fixedly secured to the graft component is lower in the first segment and third segment than in the second segment.

14. An endoprosthesis of claim 12 wherein a variation in amplitude amongst the undulations is greater in the second segment than in the first segment and third segment.

15. An endoprosthesis of claim 12 wherein the undulations along a vertical axis of the support component are more aligned in the first segment and third segment than in the second segment.

16. An endoprosthesis of claim 12 wherein the undulations along a vertical axis of the support component are more skewed in the second segment than in the first segment and third segment.

17. An endoprosthesis of claim 9 wherein the support component in the third segment comprises a series of rings and the support component in the first segment comprises a helical member.

18. An endoprosthesis of claim 9 wherein a film fixedly secures at least a portion of the support component to the graft component.

19. An endoprosthesis comprising:
a graft component and a support component defining a lumen and comprising at least a first segment, second segment, and a third segment, wherein the lumen is continuous through the first segment, second segment, and the third segment, wherein the first and third segments have greater longitudinal compressibility than the second segment; and
a stiffening member releasably coupled to the first segment.

20. The endoprosthesis of claim 19 wherein the stiffening member is releasably coupled to the third segment.

21. The endoprosthesis of claim 19 wherein the stiffening member is unattached to the second segment.

22. An endoprosthesis comprising:
a graft component and a support component defining a lumen and comprising at least a first segment, second segment, and a third segment, wherein the lumen is continuous through the first segment, second segment, and the third segment, wherein the first and third segments have greater longitudinal compressibility than the second segment,
wherein the graft component forms a series of tucks when compressed.

23. The endoprosthesis of claim 22 wherein the series of tucks are unidirectional or oriented to minimize fluid turbulence.

24. A method of repositioning an endoprosthesis comprising:
torqueing the endoprosthesis wherein the endoprosthesis comprises a graft component and a support component defining a lumen and comprising at least a first segment, second segment, and a third segment,
wherein the lumen is continuous through the first segment, second segment, and the third segment and
wherein the first and third segments have greater longitudinal compressibility than the second segment,
wherein the second segment of the endoprosthesis rotates with a minimal axial or radial deformation; and
advancing the endoprosthesis wherein the second segment advances the endoprosthesis with the minimal axial or radial deformation; or
retracting the endoprosthesis wherein the second segment retracts with the minimal axial or radial deformation.

* * * * *